US00PP22289P2

(12) United States Plant Patent
van Kleinwee

(10) Patent No.: US PP22,289 P2
(45) Date of Patent: Nov. 29, 2011

(54) *CALIBRACHOA* PLANT NAMED 'CALPRIWI'

(50) Latin Name: *Calibrachoa spp.*
Varietal Denomination: Calpriwi

(75) Inventor: Theodorus Cornelis van Kleinwee, Enkhuizen (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/806,229

(22) Filed: Aug. 6, 2010

(51) Int. Cl.
*A01H 5/00* (2006.01)

(52) U.S. Cl. ..... Plt./413

(58) Field of Classification Search ..... Plt./413
See application file for complete search history.

*Primary Examiner* — Susan McCormick Ewoldt
(74) *Attorney, Agent, or Firm* — S. Matthew Edwards

(57) ABSTRACT

A new *Calibrachoa* plant named 'Calpriwi' particularly distinguished by the cultivar has medium to large sized, white colored flower, semi-trailing plant habit, medium green foliage, is very early to flower and is more floriferous throughout the season.

1 Drawing Sheet

Latin name of the genus and species of the plant claimed: *Calibrachoa* spp.

Varietal denomination: 'Calpriwi'.

BACKGROUND OF THE NEW PLANT

The present invention comprises a new *Calibrachoa*, botanically known as *Calibrachoa* spp., and hereinafter referred to by the variety name 'Calpriwi'.

'Calpriwi' is a product of a planned breeding program. The new cultivar has medium to large sized, white colored flowers, semi-trailing plant habit, medium green foliage, is very early to flower and is more floriferous throughout the season.

'Calpriwi' originated from a hybridization made in May 2004 in a controlled breeding environment in Enkhuizen, Netherlands. The female parent was the unpatented proprietary plant designated 'E0139-1', with light pink flowers, a more trailing plant habit and is later to flower.

The male parent of 'Calpriwi' was an unpatented proprietary plant identified as 'C4458-1' with white flowers, a little more upright habit, fewer branches and is less floriferous. The resultant seed was sown in February 2005.

'Calpriwi' was selected as one flowering plant within the progeny of the stated cross in May 2005 a controlled environment in Enkhuizen, Netherlands.

The first act of asexual reproduction of 'Calpriwi' was accomplished when vegetative cuttings were propagated from the initial selection in May 2005 in a controlled environment in Enkhuizen, Netherlands.

BRIEF SUMMARY OF INVENTION

Horticultural examination of plants grown from cuttings of the plant initiated in May 2005, and continuing thereafter, has demonstrated that the combination of characteristics as herein disclosed for 'Calpriwi' are firmly fixed and are retained through successive generations of asexual reproduction.

'Calpriwi' has not been observed under all possible environmental conditions. The phenotype may vary significantly with variations in environment such as temperature, light intensity and day length.

Plant Breeder's Rights for this cultivar were applied for in Canada on Feb. 9, 2010 (#10-6822) and in CVPO on Sep. 29, 2009 (#2009/1909). 'Calpriwi' has not been made publicly available more than one year prior to the filing of this application.

The following traits have been repeatedly observed and are determined to be basic characteristics of the new variety. The combination of these characteristics distinguishes this *Calibrachoa* as a new and distinct variety.

BRIEF DESCRIPTION OF THE PHOTOGRAPHS

The accompanying photographic drawing shows typical flower and foliage characteristics of 'Calpriwi' with colors being as true as possible with an illustration of this type.

The photographic drawing shows a flowering potted plant of the new variety and a close-up of the flowers.

DETAILED BOTANICAL DESCRIPTION

The aforementioned photographs were taken in April 2010 from plants growing in a greenhouse trial in Gilroy, Calif. USA. These plants were growing in 4 inch pots and were approximately 15-16 weeks of age.

The plant descriptions and measurements were taken in mid May 2010 in Hillscheid, Germany on 9 week old plants that were growing in 12 cm pots and were grown without pinching, on benches in a greenhouse at a minimum temperature (heating temperature) of 12° C.

Color references are made to The Royal Horticultural Society Colour Chart (R.H.S.) 2001.

TABLE 1

DIFFERENCES BETWEEN THE NEW VARIETY 'CALPRIWI' AND A SIMILAR VARIETY

| | 'Calpriwi' | 'Cal White' (U.S. Plant Pat. No. 14,497) |
|---|---|---|
| Stem internode length: | Shorter | Longer |
| Pedicel length: | Slightly shorter | Slightly longer |

TABLE 1-continued

DIFFERENCES BETWEEN THE NEW VARIETY 'CALPRIWI' AND A SIMILAR VARIETY

| | 'Calpriwi' | 'Cal White' (U.S. Plant Pat. No. 14,497) |
|---|---|---|
| Foliage width: | Wider | Narrower |
| Sepal length: | Longer | Shorter |

Plant:

*Form, growth and habit.*—Initially mounding, then more spreading and decumbent, pinching enhances the number of branches.

*Plant height.*—4.5-8.0 cm.

*Plant height (inflorescence included).*—5.0-8.5 cm.

*Plant width.*—31-35 cm.

Roots:

*Number of days to initiate and produce roots.*—18-24 days at about 22 degrees C.

*Type.*—Fine, fibrous, free branching.

*Color.*—RHS N1558D.

Foliage:

*Arrangement.*—Alternate, simple.

*Immature, leaf color, upper surface.*—RHS 138A.

*Lower surface.*—Closest to RHS 138B.

*Mature, leaf color, upper surface.*—Closest to RHS 137C.

*Lower surface.*—Between RHS 138A and RHS 144B.

*Length.*—3.2-3.8 cm.

*Width.*—1.2-2.0 cm.

*Shape.*—Elliptical.

*Base shape.*—Acuminate.

*Apex shape.*—Obtuse.

*Margin.*—Entire.

*Texture, upper surface.*—Dense covered with short glandular hair.

*Lower surface.*—Dense covered with short glandular hair.

*Color of veins, upper surface.*—RHS 144A.

*Color of veins, lower surface.*—RHS 144A.

*Petiole color.*—RHS 144B.

*Length.*—0.2-0.5 cm.

*Diameter.*—0.2 cm.

*Texture.*—Short glandular hairs.

Stem:

*Quantity of main branches per plant.*—13-18.

*Color of stem.*—RHS 145A or slightly deeper.

*Length of stem.*—15-19 cm.

*Diameter.*—0.2-0.3 cm.

*Length of internodes.*—0.5-1.7 cm.

*Texture.*—Dense, mostly glandular hairs of various lengths.

*Color of pedicel.*—RHS 144B.

*Length of pedicel.*—2.0-2.3 cm.

*Diameter of pedicel.*—0.1 cm.

*Texture of pedicel.*—Densely covered with short glandular hairs.

Inflorescence:

*Type.*—Flowers solitary in upper leaf axis; flowers face mainly horizontally, mostly 5-fused lobes forming a funnel form flower. Continuous flowering throughout the Summer.

*Quantity of inflorescences per plant.*—Approximately 40-50.

*Lastingness of individual blooms on the plant.*—About 7-9 days.

*Fragrance.*—None.

Bud (just when opening/showing color):

*Color.*—Upper part RHS 150D to RHS 4D; basally RHS 150C.

*Length.*—1.8-2.4 cm.

*Width.*—0.4-0.9 cm.

*Shape.*—Oblong.

Immature inflorescence:

*Flower horizontal diameter.*—3.0-3.4 cm.

*Color petals, upper surface.*—RHS 155D but whiter.

*Color petals, lower surface.*—RHS 155A with RHS 154C mid-veins.

Mature inflorescence:

*Flower horizontal diameter.*—3.4-3.8 cm.

*Flower height (vertical).*—2.2-2.4 cm.

*Color petals, upper surface.*—RHS 155D but whiter.

*Color petals, lower surface.*—RHS 155D but whiter with RHS 150C mid-veins.

*Apex shape.*—Truncate to slightly retuse.

*Margin.*—Entire.

*Waviness of petals.*—Slight.

*Petal lobation.*—Relatively little.

*Petal texture, upper surface.*—Papillose, glabrous.

*Petal texture, lower surface.*—Papillose; very short glandular hair mostly at the margins and along the veins.

*Corolla tube color outside.*—RHS 3C to RHS 3D with RHS 150C to RHS 154C weak veins.

*Inside.*—RHS 2A to RHS 2C with slight veins of about RHS 154C becoming indistinct.

*Corolla tube length.*—1.5-1.8 cm.

*Corolla texture, outside.*—Hairs along the protruding veins.

*Inside.*—Papillose.

Sepals:

*Color, upper surface.*—RHS 137C slightly lighter basally.

*Lower surface.*—RHS 137D, slightly lighter basally.

*Length.*—1.8-2.1 cm.

*Width.*—0.4-0.5 cm.

*Shape.*—Lanceolate.

*Apex shape.*—Acute.

*Based.*—Fused.

*Margins.*—Entire.

*Texture, upper surface.*—Densely covered with short glandular hairs.

*Lower surface.*—Densely covered with short glandular hairs.

Reproductive organs:

*Pistil.*—1.

*Length.*—0.8-0.9 cm.

*Style color.*—RHS 145A.

*Style length.*—0.6-0.7 cm.

*Stigma color.*—RHS 143C.

*Stamens.*—5.

*Color of filaments.*—RHS 4D to RHS 155A.

*Length filaments.*—0.5-1.0 cm.

*Anther color.*—RHS 5C.

*Anther length.*—0.1 cm.

*Anther shape.*—Elliptical.

*Color of pollen.*—RHS 10D.

*Pollen amount.*—Moderate.

*Fertility/seed set.*—Has not been observed on this hybrid.

Disease/pest resistance: Disease/pest resistance has not been observed on this hybrid.

What is claimed is:

1. A new and distinct variety of *Calibrachoa* plant named 'Calpriwi' substantially as illustrated and described herein.

* * * * *

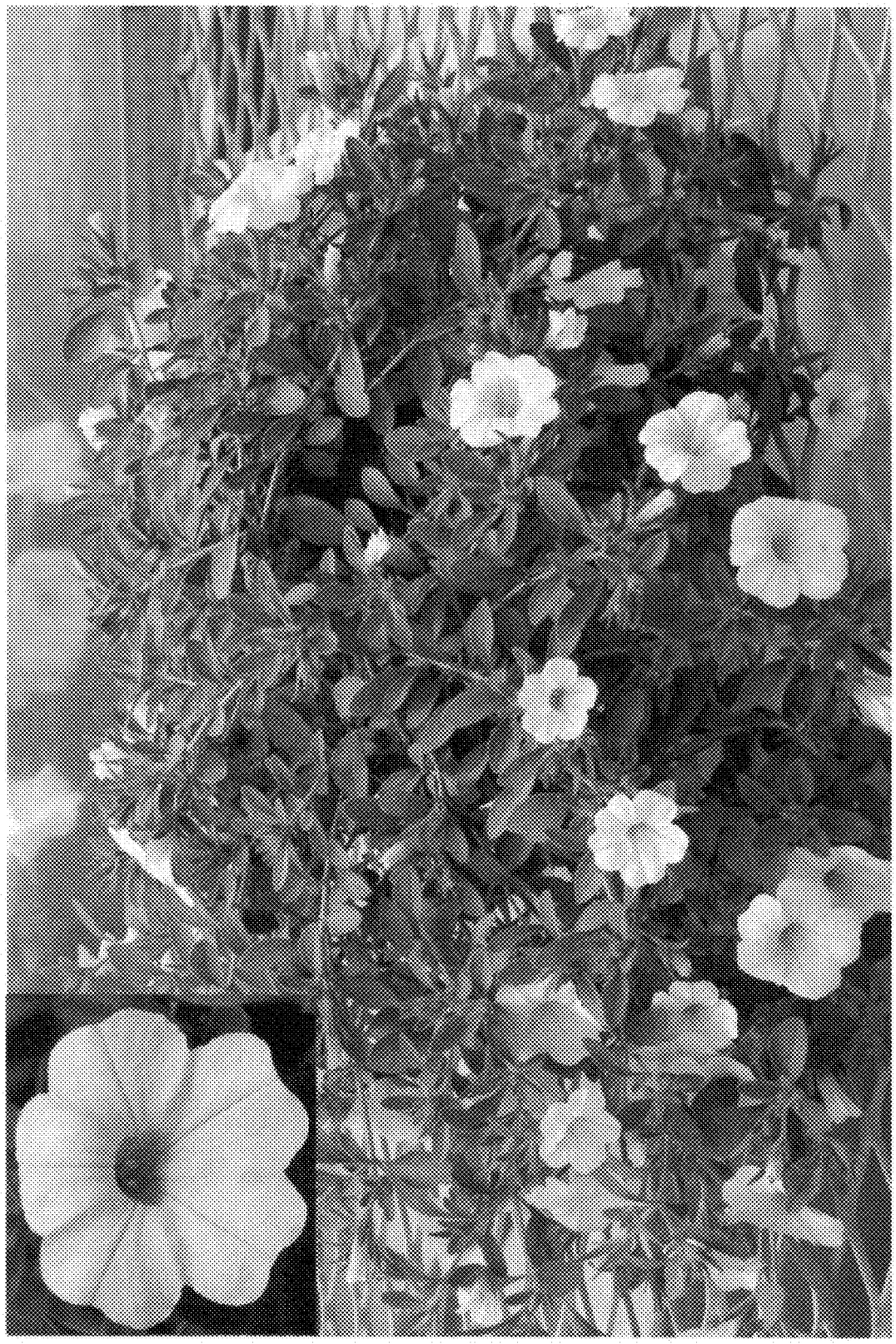

UNITED STATES PATENT AND TRADEMARK OFFICE

CERTIFICATE OF CORRECTION

PATENT NO. : PP22,289 P2
APPLICATION NO. : 12/806229
DATED : November 29, 2011
INVENTOR(S) : van Kleinwee It is certified that error appears in the above-identified patent and that said Letters Patent is hereby corrected as shown below:

At column 3, line 23, please delete "RHS N1558D" and insert therefor --RHS N155D--

Signed and Sealed this
Seventeenth Day of July, 2012

David J. Kappos

David J. Kappos
*Director of the United States Patent and Trademark Office*